United States Patent [19]

Masters et al.

[11] Patent Number: 4,740,204
[45] Date of Patent: Apr. 26, 1988

[54] SAFETY NEEDLE CAP

[76] Inventors: Edwin J. Masters, 142 Autumn, Sikeston, Mo. 63801; Paul L. Ebaugh, 1553 Lexington, Cape Girardeau, Mo. 63701

[21] Appl. No.: 943,657

[22] Filed: Dec. 18, 1986

Related U.S. Application Data

[62] Division of Ser. No. 825,524, Feb. 3, 1986, Pat. No. 4,654,034.

[51] Int. Cl.⁴ ............................................. A61M 5/32
[52] U.S. Cl. .................................... 604/192; 604/263
[58] Field of Search ............................... 604/192, 263

[56] References Cited

U.S. PATENT DOCUMENTS 4,296,786  10/1981  Brignola ...................... 604/192 X
4,629,453  12/1986  Cooper ........................... 604/192

Primary Examiner—John D. Yasko
Attorney, Agent, or Firm—Rogers, Howell, Moore & Haferkamp

[57] ABSTRACT

A safety needle cap comprising a generally cylindrical, hollow tubular body section having a closed first end and an open second end for receiving the needle, and a funnel-shaped lip surrounding the open end and projecting radially and axially outwardly to channel needles into the open end and protect fingers gripping the cap. The cap further having a guard extending from the body section intermediate the two ends to intercept needles missing the funnel-shaped lip, and positioned to space the fingers away from the open end, out of danger. The guard may be flat and disk-shaped or it may be funnel-shaped, opening toward the open end to trap errant needles.

16 Claims, 1 Drawing Sheet

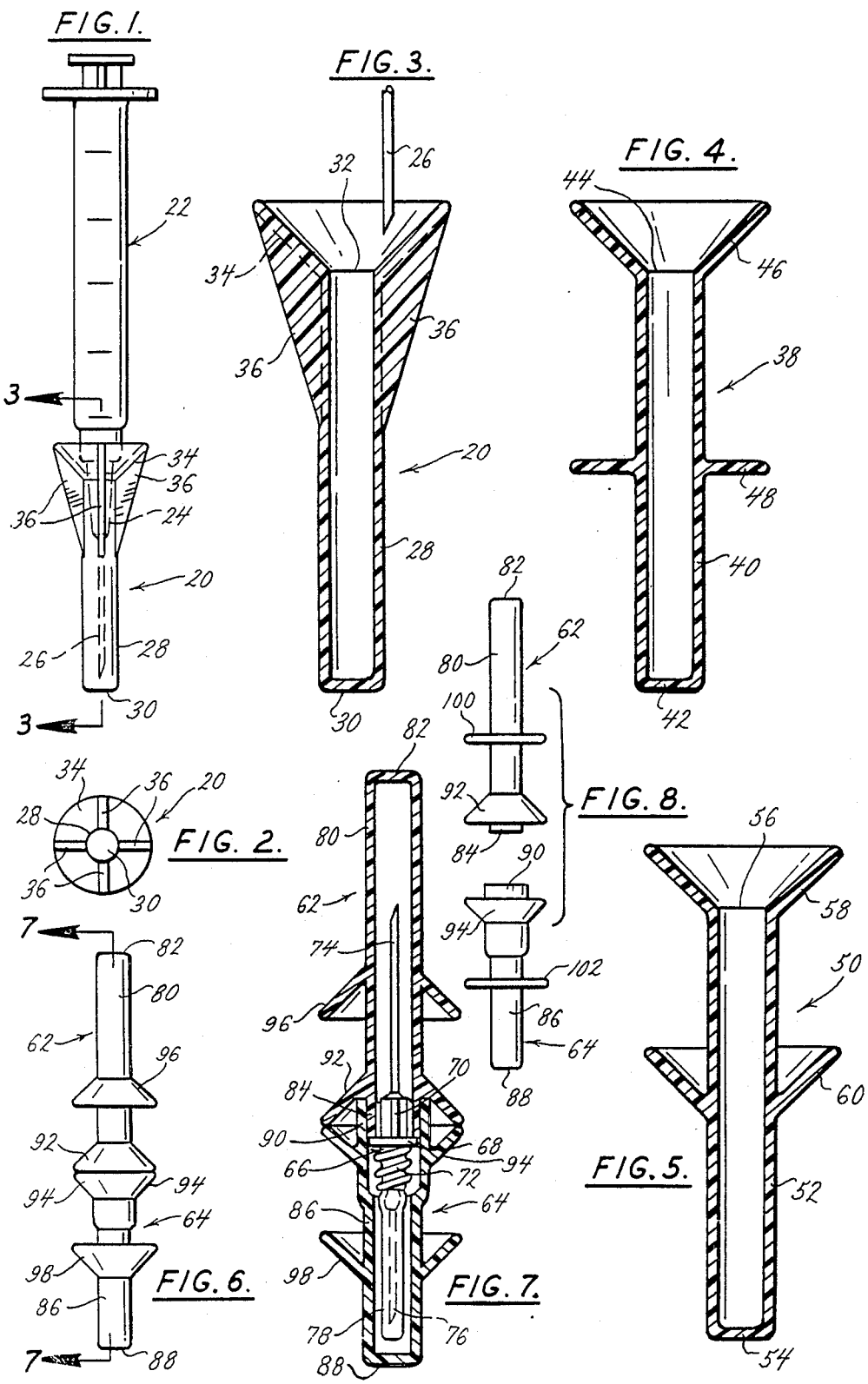

SAFETY NEEDLE CAP

This is a division of co-pending application Ser. No. 825,524, filed on Feb. 3, 1986, now U.S. Pat. No. 4,654,034.

BACKGROUND AND SUMMARY OF THE INVENTION

This invention relates to improvements in caps for hypodermic needles and in particular to a safety cap for preventing needlesticks during recapping.

Hypodermic needles, for example those used for injections or for taking blood samples, are usually equipped with a removable cap that protects and helps keep the needle sterile. The cap is usually replaceable to cover the used, contaminated needle and prevent accidental needlesticks. However, accidental needlesticks during recapping have long been a problem. Because of tension, time pressure, or fatigue, needlesticks during recapping occur with alarming frequency despite frequent warnings to be careful, and they account for the majority of accidental needlesticks. Eliminating recapping will not solve the problem because the uncapped needle is so dangerous. Indeed, a large number of accidental needlesticks are caused by uncapped needles found in beds, on floors, or in garbage cans. Even where there is a no recapping policy, the needles are often recapped because of these dangers.

Accidental needlesticks are serious because they can spread diseases, including hepatitis, venereal diseases, and of most recent concern: AIDS. A needlestick causes fear and anxiety in the victim. Both the victim and the patient may be subjected to a battery of expensive, time consuming tests. Accidental needlesticks during recapping can cost even a relatively small health care institution thousands of dollars annually. Even worse than the economic cost, however, is the transmission of disease.

For example, the victim of a needlestick from a needle contaminated by an AIDS patient must be repetitively tested for several months after the accident. It is documented that after such a needlestick, the victim may test positive for exposure to the AIDS virus, even if the disease is not contracted. A positive test would cause great fear and anxiety in the victim, would seriously disrupt the victim's personal life, and might even end the victim's ability to work in health care.

Despite the very serious nature of the problem, and the severity of the consequences, the problem has persisted for many years without any satisfactory solution. Various sheaths that can be slid down over the needle after use have been patented, for example those disclosed in U.S. Pat. Nos. 4,425,120, 3,780,734, and 2,571,654. However, these devices were too complicated and too difficult and expensive to manufacture, and have never been widely available.

A recent article Sumner, "Needlecaps to Prevent Needlestick Injuries", INFECTION CONTROL (1985) Vol. 6, No. 12. p. 495, discusses the needlestick problem and discloses a needlecap with a small, wide angle funnel surrounding the cap opening. This funnel acts as both a guide and a shield. However, inventors have found this to be only a partial solution to the very serious problem at hand. No one before the inventors has recognized the importance of spacing the user's fingers from the opening in the cap. Thus, simply enlarging the cap opening as suggested in the article is no doubt helpful in reducing needlesticks, it does not recognize the importance of spacing the user's fingers from the dangerous area adjacent the cap opening, nor does it provide any structure for accomplishing this important function.

The inventors have developed a cap that reduces the possibility of needlesticks during recapping. Like the prior caps, the cap is a generally cylindrical, hollow tube closed at one end and open at the other end to receive the needle. However, unlike the prior caps, the inventors' cap has an outwardly facing funnel-shaped lip surrounding the open end to channel an errant needle into the opening and to protect the fingers gripping the cap, combined with means to space the fingers from the opening in the cap. This spacing means can be a plurality of radial splines extending between the exterior wall of the cap and the funnel-shaped lip to support the lip and to keep the user's fingers spaced from the cap opening. Alternatively, or additionally, a guard may project radially from the cap intermediate the ends of the cap. This guard serves as a secondary protection if the needle misses the funnel-shaped lip, and is positioned to keep the user's fingers spaced from the cap opening. This guard may be a flat disk or it may be a funnel-shaped structure, opening toward the opening in the cap, which will also be able to trap an errant needle.

The cap of this invention is thus of simple and inexpensive construction, but provides a large target for the needle and safely guides the needle into the cap while protecting the user's fingers and spacing the fingers away from the opening and out of danger. The cap is adaptable to any of the needle structures presently in use including disposable syringes, TUBEX (trademark) unit dose syringes, and double pointed sample needles. This invention thus reduces the problem of accidental needlesticks during recapping at an acceptable cost.

BRIEF DESCRIPTION OF THE DRAWINGS

FIG. 1 is a side elevation view of a first embodiment of a needle cap, constructed according to the principles of this invention, as it would be installed on a hypodermic needle;

FIG. 2 is a front end view of the cap shown in FIG. 1;

FIG. 3 is a longitudinal cross-sectional view of the cap, taken along the plane of line 3—3 in FIG. 1;

FIG. 4 is a cross-sectional view of a second embodiment of a cap constructed according to the principles of this invention incorporating a disk-shaped guard;

FIG. 5 is a cross-sectional view of a third embodiment of a cap constructed according to the principles of this invention incorporating a funnel-shaped guard;

FIG. 6 is a side elevation view of two interlocking caps constructed according to the principles of this invention, as they would be installed over a double pointed sample needle;

FIG. 7 is a longitudinal cross-sectional view of the interlocking caps taken along the plane of line 7—7 in FIG. 6;

FIG. 8 is a side elevation view of a modified embodiment of the two interlocking caps, showing the caps separated, the modified embodiment having disk-shaped guards.

DETAILED DESCRIPTION OF THE PREFERRED EMBODIMENTS

A first embodiment of a needle cap constructed according to the principles of this invention, indicated generally as 20 in FIG. 1, is shown as it would be mounted on a syringe 22. Syringe 22 has a tip 24 in which needle 26 is mounted.

Cap 20 comprises a generally cylindrical, hollow tubular body section 28. The front end 30 of cap 20 is closed. The rear end 32 of cap 20 is open to receive tip 24 and needle 26 of syringe 22. When cap 20 is properly seated on syringe 22, the cap 20 covers and frictionally engages tip 24.

A funnel-shaped lip 34 surrounds the opening in rear end 32 of cap 20, projecting radially outwardly and rearwardly from body section 28 so that the funnel tapers toward the opening. Lip 34 provides a large target for needle 26 during recapping and the funnel-shape of lip 34 helps channel the needle 26 into cap 20. As shown in FIG. 3, an errant needle 26 will be channeled into cap 20 by lip 34. Lip 34 also serves to protect the fingers gripping cap 20.

As shown in FIGS. 1-3, generally triangular-shaped radial splines 36 extend between body 28 and lip 34. Splines 36 help stiffen and strengthen lip 34. The splines 36 also make it difficult to grip the cap near open end 32. Splines 36 thus help to space the user's fingers from the open end 32 of cap 20, out of danger, and thereby reduce the chance for an accidental needlestick.

Lip 34 of cap 20 can be sized or made sufficiently flexible so that the cap can be used on TUBEX (trademark) unit dose cartridges and inserted and removed from the syringe device. For this purpose lip 34 would preferably be flexible and have a diameter of about 9 mm.

A second embodiment of a needle cap constructed according to the principles of this invention is indicated generally as 38 in FIG. 4. Cap 38 is generally similar to cap 20, comprising a generally cylindrical, hollow tubular body section 40, having a closed front end 42 and an open rear end 44. A funnel-shaped lip 46 surrounds the opening in rear end 44 of cap 38. However unlike cap 20, cap 38 has a disk-shaped guard 48 projecting radially from body section 40 intermediate the ends. Guard 48 serves as a secondary protection if the needle misses funnel-shaped lip 46. Guard 48 is positioned so that it is difficult to grip cap 38 between lip 46 and guard 48. Guard 48 thus helps to space the user's fingers from the open end 44 of cap 38, out of danger, and thereby reduce the chance for an accidental needlestick.

A third embodiment of a needle cap constructed according to the principles of this invention is indicated generally as 50 in FIG. 5. Cap 50 is generally similar to cap 20, comprising a generally cylindrical, hollow tubular body section 52, having a closed front end 54 and an open rear end 56. A funnel-shaped lip 58 surrounds the opening in rear end 56 of cap 50. However unlike cap 20, cap 50 has a funnel-shaped guard 60, opening toward the open end 56, and projecting from body section 52 intermediate the ends. Guard 60 serves as a secondary protection if the needle misses funnel-shaped lip 58. The funnel-shape of guard 60 helps trap an errant needle. Guard 60 is positioned so that it is difficult to grip cap 50 between lip 58 and guard 60. Guard 60 thus helps to space the user's fingers from the open end 56 of cap 50, out of danger, and thereby reduce the chance for an accidental needlestick. If desired, either the disk-shaped guard 48 or funnel-shaped guard 60 could also be used in conjunction with cap 20 of the first embodiment having the radial splines 36.

For a standard disposable syringe it is preferable that the diameter of the lip and the guard be less than the fingergrip on the syringe. Thus the funnel-shaped lip and the guard preferably have a diameter of less than about 1 cm.

A fourth embodiment of needle caps constructed according to the principles of this invention are indicated generally as 62 and 64 in FIGS. 6-7 as they would be installed over a double pointed sample needle 66. These sample needles 66 are well known in the art and as shown in FIG. 7 comprise a base 68 having a ribbed section 70 and a threaded section 72. A needle 74 extends from ribbed section 70. A needle 76 extends from threaded section 72. Needle 76 is covered with a rubber sheath 78.

As well known in the art, cap 62 comprises a generally cylindrical, hollow tubular body section 80. The front end 82 of cap 62 is closed and the rear end 84 of cap 62 is open to receive needle 76 and ribbed section 70. When cap 62 is properly seated on sample needle 66, cap 62 covers and frictionally engages ribbed section 70.

Also, as well known in the art, cap 64 comprises a generally cylindrical, hollow tubular body section 86. The front end 88 of cap 64 is closed and the rear end 90 is open to receive the rear end 84 of needle cover 62. When cap 64 is properly seated on sample needle cover 66, cap 64 covers and frictionally engages the rear end of cap 62.

However, unlike the caps known in the art, cap 62 and cap 64 have funnel-shaped lips 92 and 94, respectively. Lips 92 and 94 open toward the open end in their respective caps, and are slightly offset from the ends of the caps. Thus when the caps 62 and 64 are properly mounted on needle 66, the lips 92 and 94 face each other with their edges touching. Lips 92 and 94 provide a large target for the needles during recapping and help protect the fingers gripping the cap. The funnel shape of lips 92 and 94 helps to trap an errant needle between the guard and the cap wall. In addition, as shown in FIGS. 6 and 7, caps 62 and 64 have funnel-shaped guards 96 and 98, respectively. Each guard 96 and 98 opens toward the opening in its respective cap. Each guard 96 and 98 serves as a secondary protection if the needle misses the funnel-shaped lip on the cap. The funnel-shape of the guards 96 and 98 helps trap errant needles. Guards 96 and 98 are positioned on their respective caps so that it is difficult to grip the cap between the funnel-shaped lip and the guard. Guards 96 and 98 thus help to space the user's fingers from the open end of the cap. thereby reducing the chance for an accidental needlestick. As shown in FIG. 8, instead of funnel-shaped guards 96 and 98, caps 62 and 64 can have disk-shaped guards 100 and 102 respectively. Guards 100 and 102 serve as a secondary protection if the needle misses the funnel-shaped lip on the cap. Guards 100 and 102, like guards 96 and 98, are positioned to help space the user's fingers from the open end of the cap, out of danger, and thereby reduce the chance for an accidental needlestick.

In use, cap 64 is removed and a special reuseable shield (not shown) is threaded onto threaded section 72. Cap 62 is removed and needle 74 is inserted into the patient. A specimen bottle (not shown) is positioned in the shield, and punctured by needle 76. After the speciment bottle is filled, it is removed from the shield. Needle 74 is removed from the patient and must be recapped with cap 62 before the shield can be removed from specimen needle 66. Needle 74 is thus inserted into the open rear end 84 of cap 62. Lip 92 and either guard 96 or 100 protect the user's fingers gripping the cap 72, space the user's fingers from the open end, and help to trap errant needles that miss the open end 84.

There are various changes and modifications which may be made to the invention as would be apparent to those skilled in the art. However, these changes or modifications are included in the teaching of the disclosure, and it is intended that the invention be limited only by the scope of the claims appended hereto.

We claim:

1. An improved needle cap of the type comprising a generally cylindrical hollow tubular body section, having a closed first end and an open second end for receiving the needle, the improvement comprising:
   a funnel-shaped lip surrounding the opening in the second end, and projecting radially and axially from the second end, in combination with means for spacing the user's fingers from the second end of the cap, the said means comprising a guard extending from the body section intermediate the ends, the guard positioned sufficiently close to the funnel-shaped lip that the cap cannot be gripped between the guard and the lip.

2. The improved needle cap of claim 1 wherein the means for spacing the user's fingers from the second end of the cap comprises a guard extending from the body section intermediate the ends, the guard positioned sufficiently close to the funnel-shaped lip that the cap cannot be gripped between the guard and the lip.

3. The improved needle cap of claim 1 wherein the guard is disk-shaped, extending radially from the body section.

4. The improved needle cap of claim 1 wherein the guard is funnel-shaped, opening toward the open end in the cap.

5. An improved pair of interlocking caps for a double pointed sample needle, the caps comprising:
   a first cap having a generally cylindrical, hollow tubular body section having a closed first end and an open second end for receiving one of the needles; and
   a second cap having a generally cylindrical, hollow tubular body section having a closed first end and an open second end, the opening in the second end of the second cap receiving and engaging the second end of the first cap;
   the improvement comprising a funnel-shaped lip on each cap, each lip opening toward the open end in its respective cap, each lip being offset from its respective open end so that when the first cap is received and engaged in the second cap the funnel-shaped lips face each other in abutting relationship, and a guard on each cap extending from the body section intermediate the ends, each guard positioned sufficiently close to the funnel-shaped lip that the cap cannot be gripped between the guard and the lip.

6. The improved pair of interlocking caps of claim 5 wherein the guard on each cap is funnel-shaped, opening towards the open end in its respective cap.

7. The improved pair of interlocking caps of claim 5 wherein the guard on each cap is generally flat and disk-shaped.

8. A safety needle cap comprising a generally cylindrical, hollow tubular body section, having a closed first end, an open second end for receiving the needle, and a funnel-shaped lip surrounding the open end and projecting radially and axially outwardly from the open end to channel needles into the open end, the lip projecting radially outwardly sufficiently to protect fingers gripping the cap, and a guard extending from the body section intermediate the two ends to intercept needles missing the funnel-shaped lip, the guard positioned sufficiently close to the lip to prevent the user from gripping the cap between the lip and the guard.

9. The needle cap of claim 8 wherein the guard is generally flat and disk-shaped.

10. The needle cap of claim 8 wherein the guard is funnel-shaped, and opens toward the open end in the cap.

11. An improved needle cap of the type comprising a generally cylindrical hollow tubular body section, having a closed first end and an open second end for receiving the needle, the improvement comprising:
   (a) a funnel-shaped lip surrounding the opening in the second end, and projecting radially and axially from the second end, in combination with means for spacing the user's fingers from the second end of the cap, the said means comprising a funnel-shaped guard extending from the body section intermediate the ends, the guard opening toward the open end of the cap, the guard positioned sufficiently close to the funnel-shaped lip that it is difficult to grip the cap between the guard and the lip.

12. A safety needle cap comprising a generally cylindrical, hollow tubular body section, having a closed first end, an open second end for receiving the needle, and a funnel-shaped lip surrounding the open end and projecting radially and axially outwardly from the open end to channel needles into the open end, the lip projecting radially outwardly sufficiently to protect fingers gripping the cap, and a guard extending from the body section intermediate the two ends to intercept needles missing the funnel-shaped lip, the guard being funnel-shaped and opening toward the open end in the cap, the guard positioned sufficiently close to the lip to make it difficult for the user to grip the cap between the lip and the guard.

13. An improved needle cap of the type comprising a generally cylindrical hollow tubular body section, having a closed first end and an open second end for receiving the needle, the improvement comprising:
   (a) A funnel-shaped lip surrounding the opening in the second end, and projecting radially and axially from the second end, in combination with means for spacing the user's fingers from the second end of the cap, the said means comprising a projecting fin-shaped guard projecting outwardly from the body section intermediate the ends.

14. The needle cap of claim 13 wherein the distance of outward projection of the fin-shaped guard from the axis of the tubular body is at least substantially the same as the distance of outward projection of the lip from the said axis.

15. A safety needle cap comprising a generally cylindrical, hollow tubular body section, having a closed first end, and an open second end for receiving the needle, and a funnel-shaped lip surrounding the open end and projecting radially and axially outwardly from the open end to channel needles into the open end, the lip projecting radially outwardly sufficiently to protect fingers gripping the cap, and a fin-shaped guard extending from the body section intermediate the two ends to intercept needles missing the funnel-shaped lip and to space a user's hand from the open end of the cap.

16. The safety needle cap of claim 13 wherein the fin-shaped guard projects outwardly from the axis of the body section a distance which is at least substantially the same distance as the distance of outward projection of the lip from the said axis.

* * * * *